United States Patent [19]

Tang

[11] 4,308,375
[45] Dec. 29, 1981

[54] METHOD FOR PURIFYING WATER-INSOLUBLE POLYENE ANTIBIOTICS

[75] Inventor: William W. Tang, Mercerville, N.J.

[73] Assignee: E. R. Squibb & Sons, Inc., Princeton, N.J.

[21] Appl. No.: 194,516

[22] Filed: Oct. 6, 1980

[51] Int. Cl.$^3$ ............................................ C07H 17/08
[52] U.S. Cl. .................................... 536/17 R; 424/180
[58] Field of Search ............................ 536/17 R, 17 C

[56] References Cited

U.S. PATENT DOCUMENTS 3,945,993  3/1976  Schaffner et al. ................. 536/17 C
4,177,265  12/1979  Michel et al. ...................... 536/17 C

OTHER PUBLICATIONS

Slejko, Chem. Absts., 90:76094n, p. 251 (1979), "Removal of Biological Matter from Aqueous Streams Via Ion Exchange Filtration".
Schubert, Chem. Absts., 85:83086m, p. 333 (1976), "On Bacterial Aftergrowth in Drinking and Industrial Water II. Apparative and Processing Effects on the Growth of Bacteria and the Possibility of Disinfection on Ion Exchange Resin Systems".
Kuehne, Chem. Absts., 74:130263b, p. 318 (1971), "Ion Exchange or Activated Charcoal Filter Contaminated with Microbial Impurities".
Rohm and Haas Co., Chem. Absts., 91:198601s, p. 354 (1979), "Bacteria Removal from Liquid Media by Ion Exchange Column".
Semmens, Chem. Absts., 90:11888e, p. 342 (1979), "Water Purification Process".
Ogoshi, Chem. Absts., 90:192358a, p. 350 (1979), "Ultrapure Water".

Primary Examiner—Johnnie R. Brown
Attorney, Agent, or Firm—Lawrence S. Levinson; Burton Rodney

[57] ABSTRACT

A method for purifying water-insoluble polyene antibiotics, such as amphotericin and nystatin, is provided which method includes the step of passing a mixture of the polyene antibiotic dispersed in methanol through an ion exchange column whereby gram positive and gram negative bacteria are removed from the antibiotic.

13 Claims, No Drawings

METHOD FOR PURIFYING WATER-INSOLUBLE POLYENE ANTIBIOTICS

FIELD OF THE INVENTION

The present invention relates to a method for purifying antibiotics, such as amphotericin B or nystatin, by passing the antibiotic through an ion exchange column.

BACKGROUND OF THE INVENTION

In the manufacture of polyene antibiotics, such as amphotercin B and nystatin, broth containing the antibiotic is filtered to remove the antibiotic solids, the solids are extracted with acidified methanol, the pH of the antibiotic rich methanol is raised to a convenient level, and the antibiotic is crystallized from the methanol. The crystals may then be formulated to produce topical creams and ointments.

DESCRIPTION OF THE INVENTION

In accordance with the present invention, the above-described purification procedure is improved and enhanced by passing the antibiotic rich methanol through an ion exchange resin whereby gram positive bacteria and gram negative bacteria are substantially completely removed from the antibiotic rich methanol.

The antibiotic may then be crystallized out from the so-purified antibiotic rich methanol.

The ion exchange resins suitable for use herein are of the large-pore macroreticular type and will have a density (skeletal) of within the range of from about 1 to about 1.1 g/cc and preferably about 1.04 g/cc, a porosity (cc pores/g dry resin) of within the range of from about 1.0 to about 1.6, and a mean pore diameter of within the range of from about 25,000 to about 230,000 Å. An example of such ion exchange resin includes type I quaternary ammonium anion ion exchange resin (Ambergard XE-352 resin, Rohm and Haas Company).

The antibiotic rich methanol will contain from about 1 to about 5%, and preferably from about 2 to about 3% antibiotic. It will be at a temperature within the range of from about 15° to about 25° C., and preferably from about 16° to about 18° C., and will have a pH within the range of from about 3.5 to about 4.5, and preferably from about 3.8 to about 4.0 and will be passed through the ion exchange resin at a flow rate of within the range of from about 3 to about 10 gal/min/ft$^3$ (resin bed volume), and preferably within the range of from about 7 to about 10 gal/min/ft$^3$.

It will also be appreciated that in addition to methanol, any other solvent may be employed which will substantially disperse the antibiotic. For example, where the antibiotic to be purified is amphotericin B, other solvents which may be employed in place of methanol include dimethylformamide or dimethylsulfoxide. Where the antibiotic is nystatin, other solvents which may be employed in place of methanol include dimethylformamide, ethanol or propylene glycol.

As indicated, the type of antibiotic which may be purified by the method of the present invention is of the water-insoluble polyene type, such as amphotericin B, nystatin or pleuromutilin.

In carrying out the method of the present invention for purifying amphotericin B, amphotericin B formed by fermentation (according to conventional practice) is filtered, methanol is added to form a methanol slurry containing from about 1 to about 5% amphotericin B, having a pH of from about 5.0 to about 7.0, and a specific gravity of from about 0.8 to about 0.9. The amphotericin rich methanol is then acidified with hydrochloric or other mineral acid to a pH of within the range of from about 2.0 to about 3.0, and then held in a holding tank for at least 60 minutes to allow for methanol extraction. Thereafter, the acidified amphotericin rich methanol is adjusted to a pH of from about 3.5 to about 4.5 with, for example, sodium hydroxide. The mixture is filtered and passed at room temperature through an ion exchange column containing a type I quaternary ammonium anion ion exchange resin as described hereinbefore. The column is designed so that the amphotericin rich methanol flows through the resin bed at a rate of from about 14 to about 20 gallons per minute. The resin is found to remove gram negative and gram positive bacteria from the amphotericin.

The so-purified amphotericin is then crystallized employing conventional crystallization techniques, for example, heating and cooling slowly. The so-purified crystals collected are then filtered, washed and dried.

Purification of nystatin rich methanol is carried out in a manner similar to that described for amphotericin B except that in carrying out the method of the present invention for purifying nystatin, nystatin formed by fermentation (according to conventional practice) is filtered, methanol is added to form a methanol slurry containing from about 4 to about 15% nystatin, having a pH of from about 5.0 to about 7.0, and a specific gravity of from about 0.8 to about 0.9. The nystatin rich methanol is then acidified with hydrochloric or other mineral acid to a pH of within the range of from about 3.0 to about 4.0, and then held in a holding tank for at least 30 minutes to allow for methanol extraction. Thereafter, the acidified nystatin rich methanol is adjusted to a pH of from about 5.0 to about 7.0 with, for example, sodium hydroxide. The mixture is filtered and passed at room temperature through an ion exchange column containing a type I quaternary ammonium anion ion exchange resin as described hereinbefore. The column is designed so that the nystatin rich methanol flows through the resin bed at a rate of from about 14 to about 20 gallons per minute. The resin is found to remove gram negative and gram positive bacteria from the nystatin.

The so-purified nystatin is then crystallized employing conventional crystallization techniques, for example, heating and cooling slowly. The so-purified crystals collected are then filtered, washed and dried.

The following Examples represent preferred embodiments of the present invention.

EXAMPLE 1

Purification of Amphotericin B

Amphotericin B is recovered from a standard fermentor, filtered via an Oliver rotary filter and the recovered solids slurried in methanol to form a slurry containing about 90% methanol and 10% amphotericin B. The slurry is acidified to a pH of about 2.5 and then held in a holding tank for about 60 minutes. Thereafter, sodium hydroxide is added to the mix to raise its pH to about 4.

The amphotericin rich methanol is then filtered and passed to an ion exchange column employing Ambergard XE-352 resin (Rohm and Haas) as the ion exchange resin which is a large-pore macroreticular material having a density (skeletal of 1.04 g/cc, a porosity (cc pores/g dry resin) of 1–1.6 and a mean pore diameter of 70,000 Å.

The amphotericin rich methanol enters the ion exchange column at a flow rate of 7 to 10 gpm/ft$^3$ (resin bed volume), at a temperature of 20° C. and a pH of about 4.

After a residence time of 90 seconds the amphotericin rich methanol flowing out of the ion exchange column is found to be substantially free of all gram positive and gram negative bacteria which has been adsorbed from the amphotericin by the ion exchange resin.

The so-purified amphotericin is then crystallized according to conventional techniques, and filtered, washed and dried.

EXAMPLE 2

Purification of Nystatin

Nystatin is recovered from a standard fermentor, filtered via an Oliver rotary filter and the recovered solids slurried in methanol to form a slurry containing about 90% methanol and 10% nystatin. The slurry is acidified to a pH of about 3.5 and then held in a holding tank for about 30 minutes. Thereafter, sodium hydroxide is added to the mix to raise its pH to about 6.0.

The nystatin rich methanol is then filtered and passed through an ion exchange column employing Ambergard XE-352 resin (Rohm and Haas) as the ion exchange resin which is a large-pore macroreticular material having a density (skeletal) of 1.04 g/cc, a porosity (cc pores/g dry resin) of 1–1.6 and a mean pore diameter of 70,000 Å.

The nystatin rich methanol enters the ion exchange column at a flow rate of 7 to 10 gpm/ft$^3$ (resin bed volume), at a temperature of 20° C. and a pH of about 4.

After a residence time of 90 seconds nystatin rich methanol flowing out of the ion exchange column is found to be substantially free of all gram positive and gram negative bacteria which has been adsorbed from the nystatin by the ion exchange resin.

The so-purified nystatin is then crystallized according to conventional techniques, and filtered, washed and dried.

What is claimed is:

1. A method for purifying water-insoluble polyene antibiotics, which comprises forming a slurry of the antibiotic in an appropriate solvent, passing the antibiotic-solvent mixture through an ion exchange resin to filter gram positive bacteria and gram negative bacteria from the antibiotic and recovering purified antibiotic from the ion exchange resin.

2. The method as defined in claim 1 wherein said antibiotic is amphotericin B.

3. The method as defined in claim 1 wherein said antibiotic is nystatin or pleuromutilin.

4. The method as defined in claim 1 wherein the solvent employed is methanol.

5. The method as defined in claim 1 wherein the antibiotic-solvent mixture is amphotericin B rich methanol.

6. The method as defined in claim 5 wherein the amphotericin B methanol mix has a pH of about 4 before it is passed through the ion exchange resin.

7. The method as defined in claim 2 wherein the ion exchange resin is type I quaternary ammonium anion ion exchange resin.

8. The method as defined in claim 3 wherein the ion exchange resin is type I quaternary ammonium anion ion exchange resin.

9. The method as defined in claim 1 wherein the amphotericin B rich methanol is passed through the ion exchange resin at a flow rate of from about 7 to about 10 gpm/ft$^3$ of resin bed volume.

10. The method as defined in claim 4 wherein said antibiotic-solvent mixture contains from about 1 to about 5% by weight antibiotic.

11. The method as defined in claim 10 wherein the antibiotic-solvent mixture is at a temperature of within the range of from about 15° to about 25° C.

12. The method as defined in claim 1 wherein the antibiotic-solvent mixture is at a pH within the range of from about 3.5 to about 4.5.

13. The method as defined in claim 1 wherein the antibiotic-solvent mixture is passed through the ion exchange resin at a flow rate of within the range of from about 3 to about 10 gal/min/ft$^3$ (resin bed volume).

* * * * *